United States Patent [19]
Cotrel et al.

[11] 3,987,174
[45] Oct. 19, 1976

[54] ISOINDOLIN-1-ONE DERIVATIVES

[75] Inventors: Claude Cotrel, Choisy-le-Roi; Claude Jeanmart, Brunoy; Mayer Naoum Messer, Bievres, all of France

[73] Assignee: Rhone-Poulenc S.A., Paris, France

[22] Filed: Nov. 25, 1974

[21] Appl. No.: 527,031

Related U.S. Application Data

[62] Division of Ser. No. 341,307, March 14, 1973, Pat. No. 3,898,232.

[30] Foreign Application Priority Data

Mar. 16, 1972   France .............................. 72.09207
Feb. 2, 1973    France .............................. 73.03728

[52] U.S. Cl. ............................ 424/263; 260/250 A; 260/268 TR; 260/268 PC; 260/295 K; 424/250
[51] Int. Cl.² ................ A61K 31/44; C07D 401/04
[58] Field of Search ................... 260/294.9, 295 B; 424/263

[56] References Cited
OTHER PUBLICATIONS
Cotrel, Chemical Abstracts 77:5526a (1972).

*Primary Examiner*—Norman A. Drezin
*Attorney, Agent, or Firm*—Stevens, Davis, Miller & Mosher

[57] ABSTRACT

Isoindolin-1-one derivatives substituted on the nitrogen atom in the 2-position by an unsubstituted or substituted phenyl radical or a heterocyclic radical having aromatic characteristics, substituted in the 3-position by a 3-amino(or substituted amino)-2-hydroxypropoxy group, and optionally substituted in the 5- and/or 6-positions by one or two alkoxy radicals or optionally substituted in the 5- and 6-positions by a methylenedioxy radical, possess pharmacodynamic properties, and are especially useful as anti-arrhythmic agents.

6 Claims, No Drawings

ISOINDOLIN-1-ONE DERIVATIVES

This is a division of application Ser. No. 341,307, filed Mar. 14, 1973 now U.S. Pat. No. 3,898,232.

This invention relates to new therapeutically useful isoindoline derivatives, processes for their preparation and pharmaceutical compositions containing them.

The new isoindoline derivatives of the present invention are those of the general formula:

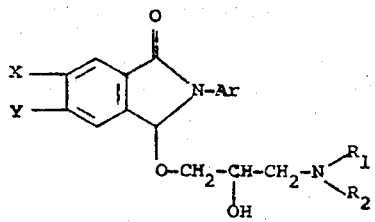
I

[wherein Ar represent a phenyl radical or a heterocyclic radical having aromatic characteristics, for example pyridyl or pyridazinyl, optionally carrying one or two substituents, which — in the latter case — may be identical or different, selected from halogen (e.g. chlorine) atoms, alkyl radicals containing 1 to 4 carbon atoms (e.g. methyl), alkoxy radicals containing 1 to 4 carbon atoms (e.g. methoxy), cyano and nitro radicals and the trifluoromethyl group, the symbols X and Y, which may have the same or different significances, each represent a hydrogen atom or an alkoxy radical containing 1 to 4 carbon atoms (preferably methoxy), or X and Y together form a methylenedioxy radical, and the symbols $R_1$ and $R_2$, which may have the same or different significances, each represent a hydrogen atom or an alkyl radical containing 1 to 4 carbon atoms, or $R_1$ and $R_2$ together with the nitrogen atom to which they are attached represent a mononuclear 5- or 6-membered heterocyclic radical, which may include a further hetero atom selected from oxygen, sulphur and nitrogen, and which may optionally carry as substituent an alkyl radical containing 1 to 4 carbon atoms, for example piperidino, morpholino, or piperazin-1-yl optionally carrying on the 4-position nitrogen atom an alkyl radical containing 1 to 4 carbon atoms (preferably methyl)], and acid addition salts thereof. It is to be understood that the aforementioned alkyl and alkoxy groups may have straight-or branched-carbon chains.

According to a feature of the invention, the isoindoline derivatives of general formula I are prepared by the process which comprises reacting an amine of the general formula:

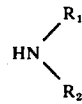
II (wherein $R_1$ and $R_2$ are as hereinbefore defined) with an isoindoline derivative of the general formula:

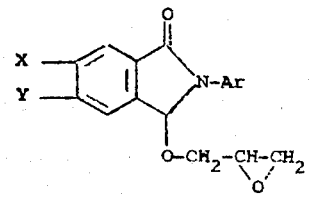
III wherein Ar, X and Y are as hereinbefore defined. The reaction is generally carried out by heating the isoindoline derivative of general formula III with the amine of general formula II at the boiling point of the reaction mixture or under pressure in an autoclave. The reaction can also be carried out by heating the reactants in an organic solvent, for example benzene or toluene.

The isoindoline derivatives of general formula III can be obtained by reacting epichlorohydrin with an alkali metal salts, optionally prepared in situ, of an isoindoline derivative of the general formula:

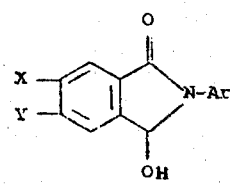
IV wherin Ar, X and Y are as hereinbefore defined. The reaction is generally carried out in an anhydrous organic solvent, for example dimethylformamide, at a temperature below 60° C.

The compounds of general formula IV can be obtained by reducing a phthalimide of the general formula:

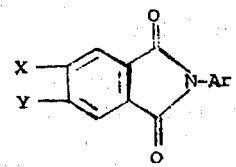
V (wherein Ar, X and Y are as hereinbefore defined) by methods known per se for reducing one of the carbonyl groups of phthalimide to a >CHOH group. The reduction is generally carried out by means of magnesium in a mixture of methanol and a saturated solution of ammonium chloride or by means of an alkali metal borohydride in an aqueous or aqueous-alcoholic medium.

When the phthalimido radical is substituted asymmetrically, the partial reduction of a compound of general formula V can lead to isomeric products which can be separated by application of physico-chemical methods such as fractional crystallisation or chromatography.

The compounds of general formula V can be obtained by reacting an amine of the general formula:

Ar — $NH_2$     VI (wherein Ar is as hereinbefore defined) with an o-phthalic acid anhydride of the general formula:

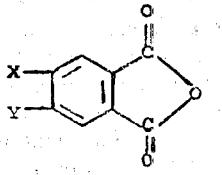
VII wherein X and Y are as hereinbefore defined.

According to another feature of the invention, the isoindoline derivatives of general formula X are prepared by the process which comprises reacting an epoxypropane of the general formula:

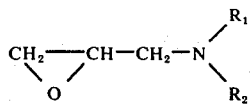  VIII (wherein $R_1$ and $R_2$ are as hereinbefore defined) with an alkali metal derivative, optionally prepared in situ, of an isoindoline derivative of general formula IV, wherein Ar, X and Y are as hereinbefore defined. The reaction is generally carried out in an anhydrous organic solvent, for example dimethylformamide, at a temperature below 30° C.

The epoxypropanes of general formula VIII can be obtained by reacting an amine of general formula II with epichlorohydrin.

The isoindoline derivatives of general formula I obtained by the aforementioned processes can be purified by physical methods such as distillation, crystallisation or chromatography, or by chemical methods such as formation of salts, crystallisation of the salts and decomposition of them in an alkaline medium. In carrying out the said chemical methods the nature of the anion of the salt is immaterial, the only requirement being that the salt must be well defined and readily crystallisable.

The isoindoline derivatives of general formula I may be converted by methods known per se into acid addition salts. The acid addition salts can be obtained by the action of acids on the new compounds in appropriate solvents. As organic solvents there may be used alcohols, ketones, ethers, or chlorinated hydrocarbons. The salt which is formed, is precipitated, if necessary after concentration of the solution, and is isolated by filtration or decantation.

By the term "methods known per se" as used in this specification is meant methods heretofore used or described in the chemical literature.

The isoindoline derivatives of the invention and their addition salts possess valuable pharmacodynamic properties; they are very active as anti-arrhythmic agents. In vitro, at concentrations of between 1 and 10 mg/liter, they have proved to be active in an investigation of the prolongation of the refractory period of auricles isolated from rabbits [G. S. Dawes, Brit. J. Pharmacol., 1, 90 (1946)]. In vivo, they have proved to be active in rabbits against cardiographic anomalies caused by aconitine and in dogs against ventricular tachyarrhythmia caused by ouabain [B. R. Lucchesi et al, J. Pharmacol., 132, 372 (1961) and Ann. N.Y. Acad. Sc., 139, art. 3, 940 (1967)] at doses between 0.1 and 10 mg/kg animal body weight when administered intravenously.

Preferred isoindoline derivatives of the invention are those of general formula I wherein the symbol Ar represents a phenyl, pyridyl (e.g. pyrid-2-yl) or pyridazinyl (e.g. pyridazin-3-yl) radical optionally substituted by a halogen (preferably chlorine) atom, an alkyl or alkoxy radical containing 1 to 4 carbon atoms (preferably methyl or methoxy) or a trifluoromethyl group, X and Y both represent hydrogen atoms or both represent methoxy groups, $R_1$ represents an alkyl radical containing 1 to 4 carbon atoms (preferably isopropyl or t.-butyl) and $R_2$ represents a hydrogen atom, or the grouping $-NR_1R_2$ represents a piperazin-1-yl radical optionally carrying in the 4-position an alkyl radical containing 1 to 4 carbon atoms (preferably methyl). Of outstanding importance are those compounds wherein Ar represents a phenyl radical, X and Y both represent hydrogen atoms, $R_1$ represents an alkyl radical containing 1 to 4 carbon atoms (preferably isopropyl or t.-butyl), and $R_2$ represents a hydrogen atom, and especially 3-(2-hydroxy-3-isopropylamino-propoxy)-2-phenyl-isoindolin-1-one and 3-(2-hydroxy-3-t.-butylamino-propoxy)-2-phenyl-isoindolin-1-one.

For therapeutic purposes, the isoindoline derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllin-acetates, salicylates, phenolphthalinates and methylene-bis-β-hydroxynaphthoates) so that the beneficial physiological properties inherent in the bases are not vitiated by side effects ascribable to the anion.

The following non-limitative Examples illustrate the invention.

EXAMPLE 1

A solution of 3-(2,3-epoxypropoxy)-2-phenyl-isoindolin-1-one (19.7 g.) in isopropylamine (50 cc.) is heated under reflux for 26 hours. After cooling the reaction mixture, di-isopropyl ether (100 cc.) is added and the product which crystallises is filtered off and then washed with di-isopropyl ether (50 cc.). After drying, a product (18.2 g.), melting at 98° C., is obtained. On recrystallisation from acetonitrile (70 cc.), 3-(2-hydroxy-3-isopropylamino-propoxy)-2-phenyl-isoindolin-1-one (14.1 g.), melting at 98° C., is obtained.

3-(2,3-Epoxypropoxy)-2-phenyl-isoindolin-1-one employed as a starting material can be prepared by adding a solution of 3-hydroxy-2-phenyl-isoindolin-1-one (67.5 g.) in anhydrous dimethylformamide (180 cc.) to a suspension of sodium hydride (50% dispersion in mineral oil) (15.8 g.) in anhydrous dimethyl-formamide (250 cc.), whilst keeping the temperature at about 30° C. When the evolution of gas has ceased, epichlorohydrin (55.5 g.) is added and the temperature is allowed to rise gradually to about 50° C. The reaction mixture is stirred for a further 5 hours, whilst allowing it to return to a temperature of about 20° C., and is then poured into water (1,500 cc.). The insoluble yellow oil is extracted three times with methylene chloride (total 800 cc.). The solution obtained is washed five times with water (total 1,250 cc.), dried over sodium sulphate and then concentrated to dryness under reduced pressure. A brown oil (85 g.) is obtained and is dissolved in a mixture of methylene chloride and cyclohexane (1/1 by volume; 500 cc.). The solution obtained is filtered through silica gel (800 g.) contained in a column 6.5 cm. in diameter. Elution is then carried out with a mixture of methylene chloride and cyclohexane (1/1 by volume; 2,500 cc.) and then with a mixture of methylene chloride and cyclohexane (3/1 by volume; 1,000 cc.). These eluates are discarded. Elution is then carried out with a mixture of methylene chloride and cyclohexane (3/1 by volume; 10,000 cc.) and then with pure methylene chloride (4,000 cc.). These eluates are combined and concentrated to dryness under reduced pressure. The residue obtained is treated with diethyl ether (150 cc.) and the insoluble product is filtered off and then washed with diethyl ether (50 cc.). After drying, 3-(2,3-epoxypropoxy)-2-phenyl-isoindolin-1-one (44.4 g.), melting at 76° C., is obtained.

3-Hydroxy-2-phenyl-isoindolin-1-one can be prepared according to the method described by A. Dunet and A. Willemart, Bull, Soc. Chim. P. 1,045 (1948).

EXAMPLE 2

A solution of 3-hydroxy-2-phenyl-isoindolin-1-one (6.75 g.) in anhydrous dimethylformamide (20 cc.) is added to a suspension of sodium hydride (50% dispersion in mineral oil) (1.48 g.) in anhydrous dimethylformamide (20 cc.). When the evolution of gas has ceased, 2,3-epoxy-1-isopropylamino-propane (3.8 g.) is added whilst keeping the temperature at about 5° C. After the end of the addition, stirring is continued for a further 24 hours at a temperature of about 20° C. and then the reaction mixture is poured into ice-water (250 cc.). The insoluble oily product is extracted with methylene chloride (3 × 100 cc.). The solution obtained is dried over sodium sulphate and then concentrated to dryness under reduced pressure. The oily residue is taken up in diethyl ether (50 cc.) and the insoluble product is filtered off and then washed with diethyl ether (30 cc.). The filtrate is then extracted with 0.5N hydrochloric acid (60 cc.). The acid solution obtained is washed with diethyl ether (20 cc.) and then rendered alkaline by the addition of 1N sodium hydroxide solution (30 cc.). The insoluble oily product is extracted with diethyl ether (2 × 50 cc.) and the solution obtained is dried over sodium sulphate and then concentrated to dryness under reduced pressure. The oily product obtained is dissolved in a mixture of diethyl ether and di-isopropyl ether (1/1 by volume; 20 cc.), and the product which crystallises is filtered off and then washed with a mixture of diethyl ether and di-isopropyl ether (1/1 by volume; 5 cc.). After drying, 3-(2-hydroxy-3-isopropylamino-propoxy)-2-phenyl-isoindolin-1-one (1.35 g.), melting at 92° C., is obtained.

2,3-Epoxy-1-isopropylamino-propane employed as a starting material can be prepared by slowly adding isopropylamine (34.8 g.) to a mixture of epichlorohydrin (55.6 g.) and water (2 cc.), at a temperature of about 30° C. The reaction mixture is stirred for a further 2 hours at a temperature of about 20° C. and then a solution of sodium hydroxide (28 g.) in water (50 cc.) is added slowly, whilst maintaining this temperature. The reaction mixture is stirred for a further hour at a temperature of about 20° C. and is then poured into water (140 cc.). The insoluble oily product is extracted with diethyl ether (3 × 50 cc.). The solution obtained is washed with water (2 × 20 cc.), dried with potassium hydroxide pellets (13 g.) and then concentrated to dryness. After distilling the residue under reduced pressure, 2,3-epoxy-1-isopropylamino-propane (5.2 g.), b.p. 62° C./32 mm.Hg, is obtained.

EXAMPLE 3

A solution of 2-(4-chlorophenyl)-3-(2,3-epoxypropoxy)-isoindolin-1-one (15 g.) and isopropyl-amine (75 cc.) in anhydrous toluene (250 cc.) is heated under reflux for 5 days. The reaction mixture is then evaporated to dryness under reduced pressure and the residue obtained is recrystallised from ethyl acetate (60 cc.). After drying, 2-(4-chlorophenyl)-3-(2-hydroxy-3-isopropylamino-propoxy)-isoindolin-1-one (13 g.), melting at 107° C., is obtained.

2-(4-Chlorophenyl)-3-(2,3-epoxypropoxy)-isoindolin-1-one employed as a starting material can be prepared by adding a solution of 2-(4-chlorophenyl)-3-hydroxy-isoindolin-1-one (24 g.) in anhydrous dimethylformamdie (180 cc.) to a suspension of sodium hydride (50% dispersion in mineral oil) (4.85 g.) in anhydrous dimethylformamide (100 cc.). When the evolution of gas has ceased, epichlorohydrin (25.5 g.) is added and the mixture is stirred for 20 hours at a temperature of about 20° C. The reaction mixture is then poured into ice-water (1,750 cc.) and the oily product which separates out is extracted with methylene chloride (4 × 200 cc.). The solution obtained is dried over sodium sulphate and then evaporated to dryness under reduced pressure. The oil thus obtained is dissolved in isopropanol (35 cc.). The product which crystallises is filtered off and then washed with isopropanol (14 cc.) and di-isopropyl ether (50 cc.). After drying 2-(4-chlorophenyl)-3-(2,3-epoxypropoxy)-isoindolin-1-one (17.4 g.), melting at 90°–92° C., is obtained.

2-(4-Chlorophenyl)-3-hydroxy-isoindolin-1-one can be prepared by adding a saturated aqueous solution of ammonium chloride (150 cc.) to a suspension of 2-(4-chlorophenyl)phthalimide (25.75 g.) and magnesium turnings (8.8 g.) in methanol (1,000 cc.). After heating the reaction mixture under reflux for 2 hours and then stirring at 20° C. for 20 hours, it is again heated to the boiling point, decolourizing charcoal (10 g.) is then added and the mixture is filtered whilst hot. After evaporating the methanol under reduced pressure, water (500 cc.) is added to the residue. A product crystallises and is filtered off and washed with water (200 cc.). After drying, a product (21.8 g.), melting at 200° C., is obtained. On recrystallisation from ethanol (350 cc.), 2-(4-chlorophenyl)-3-hydroxy-isoindolin-1-one (14.6 g.), melting at 200° C., is obtained.

2-(4-Chlorophenyl)-phthalimide can be prepared according to the method described by G. Pagani et al, Il Farmaco, Ed. Sci., 23, [5], 448 (1968).

EXAMPLE 4

A solution of 2-(3-chlorophenyl)-3-(2,3-epoxypropoxy)-isoindolin-1-one (12 g.) and isopropyl-amine (120 cc.) in anhydrous toluene (200 cc.) is heated under reflux for 5 days. The reaction mixture is then evaporated to dryness under reduced pressure and the residue obtained is recrystallised from ethyl acetate (65 cc.). After drying, 2-(3-chlorophenyl)-3-(2-hydroxy-3-isopropylamino-propoxy)-isoindolin-1-one (11.6 g.), melting at 128° C., is obtained.

2-(3-Chlorophenyl)-3-(2,3-epoxypropoxy)-isoindolin-1-one employed as a starting material can be prepared by adding a solution of 2-(3-chlorophenyl)-3-hydroxy-isoindolin-1-one (19.5 g.) in anhydrous dimethylformamide (125 cc.) to a suspension of sodium hydride (50% dispersion in mineral oil) (3.96 g.) in anhydrous dimethylformamide (150 cc.). When the evolution of gas has ceased, epichlorohydrin (21 g.) is added and the mixture is stirred for 20 hours at a temperature of about 20° C. The reaction mixture is then poured into ice-water (1,500 cc.) and the oily product which separates out is extracted with methylene chloride (3 × 400 cc.). The solution obtained is dried over sodium sulphate and then evaporated to dryness under reduced pressure. The oil thus obtained is taken up in isopropanol (40 cc.). The product which crystallises is filtered off and then washed with isopropanol (10 cc.) and di-isopropyl ether (40 cc.). After drying, 2-(3-chlorophenyl)-3-(2,3-epoxypropoxy)-isoindolin-1-one (12.4 g.), melting at 123°–125° C., is obtained.

2-(3-Chlorophenyl)-3-hydroxy-isoindolin-1-one can be prepared by adding a saturated aqueous solution of ammonium chloride (150 cc.) to a suspension of 2-(3-chlorophenyl)phthalimide (25.75 g.) and magnesium turnings (8.8 g.) in methanol (1,000 cc.). After heating under reflux for 2 hours followed by stirring at 20° C. for 20 hours, decolourizing charcoal (10 g.) is added, the mixture is filtered and the methanol is then distilled under reduced pressure. Water (500 cc.) is then added to the residue. The product which crystallises is filtered off and then washed with water (200 cc.). After drying, a product (18.9 g.), melting at 170° C., is obtained. On recrystallisation from ethanol (200 cc.), 2-(3-chlorophenyl)-3-hydroxy-isoindolin-1-one (11.5 g.), melting at 172° C., is obtained.

2-(3-Chlorophenyl)phthalimide can be prepared according to the method described by G. Pagani et al, Il Farmaco, Ed. Sci., 23, [5], 448 (1968).

EXAMPLE 5

Following the procedure of Example 3 but starting with 3-(2,3-epoxypropoxy)-2-(3-methoxyphenyl)-isoindolin-1-one (28.5 g.) and isopropylamine (142 cc.), 3-(2-hydroxy-3-isopropylamino-propoxy)-2-(3-methoxyphenyl)-isoindolin-1-one (15.7 g.), melting at 110° C., is obtained after recrystallisation from ethyl acetate.

3-(2,3-Epoxypropoxy)-2-(3-methoxyphenyl)-isoindolin-1-one, in the form of a yellow oil, can be prepared following the procedure described in Example 1 for the preparation of the similar starting material from 3-hydroxy-2-(3-methoxyphenyl)-isoindolin-1-one (20.8 g.), sodium hydride (50% dispersion in mineral oil) (4.3 g.) and epichlorohydrin (22.6 g.).

3-Hydroxy-2-(3-methoxyphenyl)isoindolin-1-one can be prepared according to the method described in the specification of Belgian Patent No. 776,682, granted to Rhone-Poulenc S.A. on an application filed Dec. 14, 1971.

EXAMPLE 6

A mixture of 3-(2,3-epoxypropoxy)-2-phenyl-isoindolin-1-one (2.8 g.) and t.-butylamine (8.4 cc.) is heated in an autoclave at 100° C. for 20 hours. (85 cc.) and the insoluble product is extracted with methylene chloride (75 cc.) The organic solution is washed with water (2 × 25 cc.) and then with 0.3N hydrochloric acid (2 × 30 cc.). The acid solution obtained is rendered alkaline by addition of 1N sodium hydroxide solution (20 cc.). The insoluble oily product is extracted with methylene chloride (2 × 35 cc.), and then the organic solution obtained is dried over sodium sulphate and concentrated to dryness under reduced pressure. After two successive recrystallisations of the resulting residue from acetone, 3-(2-hydroxy-3-t.-butylamino-propoxy)-2-phenyl-isoindolin-1-one (1.6 g.), melting at 125°–130° C., is obtained.

EXAMPLE 7

Following the procedure of Example 3 but starting with 3-(2,3-epoxypropoxy)-2-(3-trifluoromethylphenyl)-isoindolin-1-one (7.5 g.) and isopropylamine (37.5 cc.), 3-(2-hydroxy-3-isopropylamino-propoxy)-2-(3-trifluoromethylphenyl)-isoindolin-1-one (5.8 g.), melting at 125° C., is obtained after recrystallisation from acetonitrile.

3-(2,3-Epoxypropoxy)-2-(3-trifluoromethylphenyl)-isoindolin-1-one, in the form of a yellow oil, can be prepared following the procedure described in Example 1 for the preparation of the similar starting material from 3-hydroxy-2-(3-trifluoromethylphenyl)-isoindolin-1-one (16 g.), sodium hydride (50% dispersion in mineral oil) (2.88 g.) and epichlorohydrin (15 g.).

3-Hydroxy-2-(3-trifluoromethylphenyl)-iso-indolin-1-one can be prepared by adding a solution of potassium borohydride (11.3 g.) in water (93 cc.) and 1N sodium hydroxide solution (11.3 cc.) to a suspension of N-(3-trifluoromethylphenyl)-phthalimide (80.9 g.) in methanol (380 cc.), whilst keeping the temperature at about 20° C. The reaction mixture is then stirred for 18 hours at a temperature of about 20° C. The insoluble product is filtered off and then washed with ethanol (50 cc.) and petroleum ether (100 cc.). After drying, 3-hydroxy-2-(3-trifluoromethylphenyl)-isoindolin-1-one (63.9 g.), melting at 202° C., is obtained.

N-(3-Trifluoromethylphenyl)-phthalimide can be prepared according to the method described by G. Pagani et al, Il Farmaco, Ed. Sci. 23 [5], 448 (1968).

EXAMPLE 8

A solution of 3-(2,3-epoxypropoxy)-2-phenyl-isoindolin-1-one (8.4 g.) and 1-methylpiperazine (3.6 g.) in anhydrous toluene (84 cc.) is heated under reflux for 3 days. After cooling, the reaction mixture is washed with water (2 × 50 cc.) and then the organic solution is extracted with 1N hydrochloric acid (55 cc.) and water (3 × 20 cc.). The aqueous and acid solutions are combined and are rendered alkaline by addition of 1N sodium hydroxide solution (55 cc.). The oil which separates out is extracted with methylene chloride (150 cc.) and then the organic solution obtained is dried over sodium sulphate and concentrated to dryness under reduced pressure. The residual oil is dissolved in ethanol (20 cc.) and the resulting solution is added to a hot solution of fumaric acid (5.85 g.) in ethanol (80 cc.). The product which crystallises on cooling is filtered off and then washed with ethanol (30 cc.) and di-isopropyl ether (40 cc.). After drying, 3-[2-hydroxy-3-(4-methylpiperazin-1-yl)-propoxy]-2-phenyl-isoindolin-1-one acid difumarate (14.5 g.), melting at 194° C., is obtained.

EXAMPLE 9

A solution of 2-(5-chloropyrid-2-yl)-3-(2,3-epoxypropoxy)-isoindolin-1-one (11.4 g.) in isopropylamine (57 cc.) is heated under reflux for 26 hours. After cooling, the reaction mixture is concentrated to dryness under reduced pressure. On recrystallisation of the resulting residue from ethyl acetate (20 cc.), 2-(5-chloropyrid-2-yl)-3-(2-hydroxy-3-isopropylamino-propoxy)-iso-indolin-1-one (10.6 g.), melting at 107° C., is obtained.

2-(5-Chloropyrid-2-yl)-3-(2,3-epoxypropoxy)-isoindolin-1-one, melting at 123° C., can be prepared from 2-(5-chloropyrid-2-yl)-3-hydroxy-isoindolin-1-one (20.8 g.), sodium hydride (50% dispersion in mineral oil) (4.2 g.) and epichlorohydrin (14.8 g.).

2-(5-Chloropyrid-2-yl)-3-hydroxy-isoindolin-1-one can be prepared according to the method described in the specification of Belgian Patent No. 771,493 granted to Rhone-Poulenc S.A. on an application filed Aug. 14, 1971.

EXAMPLE 10

A solution of 3-(2,3-epoxypropoxy)-2-(6-methyl-pyridazin-3-yl)-isoindolin-1-one (17.4 g.) in isopropylamine (87 cc.) is heated under reflux for 26 hours. The reaction mixture is then concentrated to dryness under reduced pressure. The residual oil is dissolved in ethyl acetate (400 cc.) and the solution obtained is filtered through silica gel (400 g.) contained in a column 4 cm. in diameter. Elution is then carried out successively with pure ethyl acetate (1,200 cc.), a mixture of ethyl acetate and methanol (95/5 by volume; 3,200 cc.), a mixture of ethyl acetate and methanol (90/10 by volume; 1,600 cc.) and a mixture of ethyl acetate and methanol (80/20 by volume; 1,200 cc.). All these eluates are discarded. Elution is then carried out with a mixture of ethyl acetate and methanol (80/20 by volume; 2,800 cc.) and then with a mixture of ethyl acetate and methanol (50/50 by volume; 1,600 cc.). After concentrating these eluates to dryness and recrystallising the residue from a mixture of di-isopropyl ether and acetonitrile (85/15 by volume), 3-(2-hydroxy-3-isopropylamino-propoxy)-2-(6-methyl-pyridazin-3-yl)-isoindolin-1-one (4 g.), melting at 90° C., is obtained.

3-(2,3-Epoxypropoxy)-2-(6-methylpyridazin-3-yl)-isoindolin-1-one, melting at 110° C., can be prepared by the procedure described in Example 3 for the preparation of the similar starting material from 3-hydroxy-2-(6-methylpyridazin-3-yl)-isoindolin-1-one (18 g.), sodium hydride (50% dispersion in mineral oil) 3.95 g.) and epichlorohydrin (21 g.).

2-(6-Methylpyridazin-3-yl)-3-hydroxy-isoindolin-1-one can be prepared by adding a solution of potassium borohydride (3.64 g.) in water (29 cc.) and 1N sodium hydroxide solution (3.8 cc.) to a suspension of 3-methyl-6-phthalimido-pyridazine (21 g.) in methanol (105 cc.), whilst stirring and keeping the temperature at about 15° C. After 2 hours at 20° C., the insoluble product is filtered off and then washed with methanol (60 cc.). After drying, 2-(6-methylpyridazin-3-yl)-3-hydroxy-isoindolin-1-one (18.4 g.), melting at 232° C., is obtained.

3-Methyl-6-phthalimido-pyridazine can be prepared by heating a mixture of phthalic anhydride (14.8 g.) and 3-amino-6-methyl-pyridazine (10.9 g.) in diphenyl ether (74 cc.), for 20 minutes at a temperature of about 190° C. The reaction mixture is then allowed to return to 45° C. and di-isopropyl ether (25 cc.) is added. The product which crystallises is filtered off and then washed with di-isopropyl ether (30 cc.). After drying, 3-methyl-6-phthalimido-pyridazine (21.5 g.), melting at 214° C., is obtained.

3-Amino-6-methyl-pyridazine can be prepared according to the method described by W. G. Overend and L. F. Wiggins, J. Chem. Soc., p. 239 (1947).

EXAMPLE 11

A solution of 3-(2,3-epoxypropoxy)-5,6-dimethoxy-2-phenyl-isoindolin-1-one (4.7 g.) and isopropylamine (27.6 cc.) in toluene (15 cc.) is heated in an autoclave at 100° C. for 18 hours. After cooling, the reaction mixture is concentrated to dryness under reduced pressure. After recrystallising the resulting residue from a mixture of ethyl acetate and di-isopropylether (50/50 by volume; 40 cc.), 3-(2-hydroxy-3-isopropyl-aminopropoxy)-5,6-dimethoxy-2-phenyl-isoindolin-1-one (3 g.), melting at 110° C., is obtained.

3-(2,3-Epoxypropoxy)-5,6-dimethoxy-2-phenyl-isoindolin-1-one, melting at 142° C., can be prepared by the procedure described in Example 4 for the preparation of the similar starting material from 3-hydroxy-5,6-dimethoxy-2-phenyl-isoindolin-1-one (4.5 g.), sodium hydride (50% dispersion in mineral oil) (0.85 g.) and epichlorohydrin (4.4 g.).

3-Hydroxy-5,6-dimethoxy-2-phenyl-isoindolin-1-one, melting at 205° C., can be prepared as described in Example 3 for the preparation of 2-(4-chlorophenyl)-3-hydroxy-isoindolin-1-one, but starting with 4,5-dimethoxy-2-phenyl-phthalimide (5.7 g.) and magnesium turnings (1.8 g.) in a mixture of methanol and a saturated solution of ammonium chloride.

4,5-Dimethoxy-2-phenyl-phthalimide can be prepared by heating a solution of 4,5-dimethoxy-phthalic anhydride (15 g.) and aniline (6.7 g.) in acetic acid (150 cc), under reflux for 1 hour. The product which crystallises on cooling is filtered off and then washed with di-isopropyl ether (50 cc.). After drying 4,5-dimethoxy-2-phenyl-phthalimide (18.8 g.), melting at 245° C., is obtained.

4,5-Dimethoxy-phthalic anhydride can be prepared according to the method described by G. A. Edwards et al, J. Chem. Soc., 195 (1925).

The present invention includes within its scope pharmaceutical compositions comprising, as active ingredient, at least one isoindoline derivative of general formula I, or a non-toxic acid addition salt thereof, in association with a pharmaceutical carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally to an adult should generally give does between 50 mg. and 1000 mg. of active substance per day. In general the physician will decide the posology considered appropriate, taking into account the age and weight and other factors intrinsic to the patient being treated.

The following Example illustrate pharmaceutical compositions according to the invention.

EXAMPLE 12

Tablets containing 25 mg. of active product and having the following composition are prepared in accordance with the usual technique:

| | |
|---|---|
| 3-(2-hydroxy-3-isopropylamino-propoxy)-2-phenyl-isoindolin-1-one | 0.025 g. |
| starch | 0.100 g. |
| precipitated silica | 0.022 g. |
| magnesium stearate | 0.003 g. |

We claim:
1. An isoindoline of the formula:

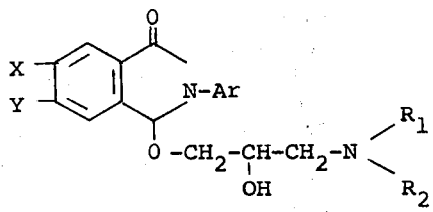

wherein Ar is pyridyl, unsubstituted or substituted by one or two substituents selected from halogen, alkyl of 1 through 4 carbon atoms, alkoxy of 1 through 4 carbon atoms, cyano, nitro and trifluoromethyl, X and Y when taken singly represent hydrogen or alkoxy of 1 through 4 carbon atoms, or X and Y when taken together represent methylenedioxy, and $R_1$ and $R_2$ represent hydrogen or alkyl of 1 through 4 carbon atoms, or a non-toxic pharmaceutically acceptable acid addition salt thereof.

2. An isoindoline according to claim 1 wherein Ar is pyridyl unsubstituted or substituted by halogen, alkyl of 1 through 4 carbon atoms, alkoxy of 1 through 4 carbon atoms or trifluoromethyl, X and Y both represent hydrogen or both represent methoxy, $R_1$ represents alkyl of 1 through 4 carbon atoms and $R_2$ represents hydrogen, or a non-toxic pharmaceutically acceptable acid addition salt thereof.

3. An isoindoline derivative according to claim 1 wherein the substituent or substituents on the radical represented by the symbol Ar is, or are, selected from chlorine, methyl, methoxy and trifluoromethyl, or a non-toxic pharmaceutically acceptable acid addition salt thereof.

4. An isoindoline derivative according to claim 1 wherein $R_1$ represents isopropyl or t.-butyl and $R_2$ represents hydrogen.

5. The isoindoline derivative according to claim 1 which is 2-(5-chloropyrid-2-yl)-3-(2-hydroxy-3-isopropylamino-propoxy)-isoindolin-1-one or a non-toxic pharmaceutically acceptable acid addition salt thereof.

6. A pharmaceutical composition useful as an antiarrhythmic which comprises, as active ingredient, an effective amount of an isoindoline of claim 1, or a non-toxic pharmaceutically acceptable acid addition salt thereof, in association with a significant amount of a pharmaceutically acceptable carrier.

* * * * *